United States Patent [19]

Whittaker et al.

[11] 4,257,857
[45] Mar. 24, 1981

[54] LIQUID PHASE PREPARATION OF 2-CHLORO-5-TRIFLUOROMETHYLPYRIDINE AND 2-CHLORO-5-PERCHLOROFLUOROMETHYLPYRIDINE

[75] Inventors: Graham Whittaker; Anne O'Brien, both of Frodsham, England

[73] Assignee: Imperial Chemical Industries Limited, London, England

[21] Appl. No.: 95,679

[22] Filed: Nov. 19, 1979

[30] Foreign Application Priority Data

Jan. 22, 1979 [GB] United Kingdom ............... 02196/79

[51] Int. Cl.³ .................... B01J 19/08; C07D 213/26
[52] U.S. Cl. ............................ 204/158 HA; 546/345
[58] Field of Search ................. 546/345; 204/158 HA

[56] References Cited

U.S. PATENT DOCUMENTS

| 3,173,919 | 3/1965 | Johnston et al. | 204/158 HA |
| 3,418,323 | 12/1968 | Johnston et al. | 204/158 HA |

*Primary Examiner*—Alan L. Rotman
*Attorney, Agent, or Firm*—Cushman, Darby & Cushman

[57] ABSTRACT

2-Chloro-5-trifluoromethylpyridine or a 2-Chloro-5-perchlorofluoromethylpyridine is prepared by chlorination of 3-trifluoromethylpyridine or a 3-perchlorofluoromethylpyridine respectively in the liquid phase in the presence of ultra-violet radiation and/or in the presence of a free-radical initiator.

10 Claims, No Drawings

LIQUID PHASE PREPARATION OF 2-CHLORO-5-TRIFLUOROMETHYLPYRIDINE AND 2-CHLORO-5-PERCHLOROFLUOROMETHYL-PYRIDINE

This invention relates to the preparation of 2-chloro-5-trifluoromethylpyridine and 2-chloro-5-perchlorofluoromethylpyridines.

2-chloro-5-trifluoromethylpyridine and 2-chloro-5-perchlorofluoromethylpyridines are desirable intermediates for use in the preparation of compounds having herbicidal activity, for example in the preparation of herbicidal pyridine compounds described in U.K. Application Ser. No. 2,002,368A.

In co-pending U.S. Application Ser. No. 010,598 is described a method of partial chlorination of 3-methylpyridine to give products containing a single chlorine atom in the pyridine ring and either two or three chlorine atoms as substituents in the methyl group. Among the products of the process there described is 2-chloro-5-trichloromethylpyridine, which may subsequently be fluorinated to yield 2-chloro-5-trifluoromethylpyridine or 2-chloro-5-perchlorofluoromethylpyridines (for example 2-chloro-5-chlorodifluoromethylpyridine).

In the partial chlorination of 3-methyl pyridine the desired 2-chloro-5-trichloromethylpyridine is, however, accompanied by substantial proportions of other partially-chlorinated derivatives which it can be difficult to separate from the desired product; this may lead to waste of material in the route to 2-chloro-5-trifluoromethylpyridine or 2-chloro-5-perchlorofluoromethylpyridines from 3-methylpyridine via 2-chloro-5-trichloromethylpyridine.

We have now found that 2-chloro-5-trifluoromethylpyridine and 2-chloro-5-perchlorofluoromethylpyridines may selectively be prepared by chlorination of 3-trifluoromethylpyridine or a 3-perchlorofluoromethylpyridine respectively. Furthermore, the separation of the desired product from the by-products may usually be achieved more readily than separation of 2-chloro-5-trichloromethylpyridine from the by-products obtained in the chlorination of 3-methylpyridine.

According to the present invention there is provided a process for the preparation of 2-chloro-5-trifluoromethylpyridine or a 2-chloro-5-perchlorofluoromethylpyridine characterised in that 3-trifluoromethylpyridine or a 3-perchlorofluoromethylpyridine respectively is chlorinated in the liquid phase in the presence of ultraviolet radiation and/or in the presence of a free-radical initiator.

The chlorination is preferably carried out in the presence of an organic diluent; this is preferably a compound which is inert towards chlorine (for example carbon tetrachloride, which is the diluent especially preferred) or a compound such that any reaction with chlorine yields a product which is inert to further chlorination (for example chloroform, which may yield carbon tetrachlorine).

The liquid-phase chlorination may be carried out over a wide range of temperature, depending partly upon the solvent employed. In general, the reaction is conveniently carried out at a temperature in the range from 0° C. to 100° C., especially from 20° C. to 80° C., and conveniently under conditions of reflux. Superatmospheric pressure may be used if desired or if necessary in order to maintain the reaction mixture in the liquid phase. Suitable free-radical initiators include peroxides (for example dibenzoyl peroxide; di-tertiary-butyl peroxide), azonitriles (for example alpha, alpha-azobisisobutyronitrile) and halides of transition metals.

It will be understood that under some circumstances, for example when reflux conditions are employed, the desired chlorination process may occur both in the liquid phase and in the vapour phase.

The desired 2-chloro-5-trifluoromethylpyridine or 2-chloro-5-perchlorofluoromethylpyridine may be recovered from the reaction products by methods conventional in the art, for example fractional distillation and fractional crystallization.

The invention is illustrated by the following Examples.

EXAMPLE 1

5 grams of 3-trifluoromethylpyridine were dissolved in 150 grams of carbon tetrachloride. The solution was heated to reflux and maintained under reflux while chlorine was continuously bubbled through the solution. Alpha, alphaazobis-isobutyronitrile was added in portions of 100 mg every hour. After 15 hours, analysis by gas-liquid chromatography showed that the major product was 2-chloro-5-trifluoromethylpyridine.

EXAMPLE 2

3.2 grams of 3-trifluoromethylpyridine were dissolved in 100 ml of carbon tetrachloride. The solution was saturated with chlorine and heated under reflux while being subjected to irradiation by a mercury-vapour lamp. After a total reaction time of 8 hours analysis by gas-liquid chromatography showed that the major product was 2-chloro-5-trifluoromethylpyridine. This was confirmed by 19 F nuclear magnetic resonance, which showed that 50% of the 3-trifluoromethylpyridine had reacted and that the product contained 7 moles of 2-chloro-5-trifluoromethylpyridine per mole of 2-chloro-3-trifluoromethylpyridine with very little 2,6-dichloro-3-trifluoromethylpyridine.

What is claimed is:

1. A process for the selective preparation of 2-chloro-5-trifluoromethylpyridine or a 2-chloro-5-perchlorofluoromethylpyridine which comprises chlorinating 3-trifluoromethylpyridine or a 3-perchlorofluoromethylpyridine respectively in the liquid phase by contacting the 3-trifluoromethylpyridine or a 3-perchlorofluoromethylpyridine respectively with chlorine in the presence of ultraviolet radiation and a liquid organic diluent solvent.

2. A process according to claim 1 wherein the reaction is carried out at a temperature in the range from 0° C. to 100° C.

3. A process according to claim 2 wherein the process is carried out at a temperature in the range from 20° C. to 80° C.

4. A process according to claim 1, wherein said 3-trifluoromethylpyridine or said 3-perchlorofluoromethylpyridine is dissolved in a liquid organic diluent solvent which is inert towards chlorine.

5. A process according to claim 4, wherein said solvent is carbon tetrachloride.

6. A process according to claim 4, wherein said chlorine is bubbled through said solvent.

7. A process according to claim 4, wherein said solvent is saturated with said chlorine.

8. A process according to claim 1, wherein 3-trifluoromethylpyridine is chlorinated to form 2-chloro-5-trifluoromethylpyridine.

9. A process according to claim 1, wherein 3-chlorodifluoromethylpyridine is chlorinated to form 2-chloro-5-chlorodifluoromethylpyridine.

10. A process according to claim 1, wherein 3-dichlorofluoromethylpyridine is chlorinated to form 2-chloro-5-dichlorofluoromethylpyridine.

* * * * *